US 8,708,961 B2

(12) United States Patent
Field et al.

(10) Patent No.: US 8,708,961 B2
(45) Date of Patent: Apr. 29, 2014

(54) APPARATUS FOR INFUSING LIQUID TO A BODY

(75) Inventors: Jeffrey F. Field, Camarillo, CA (US); April A. Marano-Ford, Manhattan Beach, CA (US); Peter R. Rule, Los Altos Hills, CA (US); Kevin J. O'Hara, Evergreen, CO (US); Thomas Allen Knotts, Mountain View, CA (US)

(73) Assignee: Medsolve Technologies, Inc., Manhattan Beach, CA (US)

( * ) Notice: Subject to any disclaimer, the term of this patent is extended or adjusted under 35 U.S.C. 154(b) by 462 days.

(21) Appl. No.: 12/021,164

(22) Filed: Jan. 28, 2008

(65) Prior Publication Data

US 2010/0331826 A1    Dec. 30, 2010

(51) Int. Cl.
*A61M 1/00* (2006.01)
(52) U.S. Cl.
USPC ........... 604/152; 604/131; 604/151; 604/153; 604/890.1; 604/891.1
(58) Field of Classification Search
USPC ................... 604/151–153, 890.1, 131, 891.1; 310/328, 348, 353, 354, 324, 330; 417/413.2–413.3, 413.1
See application file for complete search history.

(56) References Cited

U.S. PATENT DOCUMENTS

| 4,221,219 A | 9/1980 | Tucker ........................... 128/260 |
| 4,231,019 A | 10/1980 | Junginger et al. ........ 340/171 R |

(Continued)

FOREIGN PATENT DOCUMENTS

EP    1 837 787    9/2007

OTHER PUBLICATIONS

Official Action mailed Jan. 8, 2009 in companion U.S. Appl. No. 11/618,682, filed Dec. 29, 2006.
PCT Application No. PCT/US2007/86835 filed Dec. 7, 2007.

(Continued)

*Primary Examiner* — Bhisma Mehta
*Assistant Examiner* — Larry R Wilson
(74) *Attorney, Agent, or Firm* — Novak Druce Connolly Bove + Quigg LLP (57) ABSTRACT

An infusion device having a housing with a reusable control portion and an expendable reservoir portion includes a precise drive for an infusion pump. The drive includes a piezoelectric bender assembly, a limiter and at least one contact stop. The piezoelectric bender assembly includes a cantilevered piezoelectric bender having an member of predetermined thickness fixed to move with the second end. A limiter of dimensionally stable material including a gap and at least a first mounting hole extending to the gap. The member of predetermined thickness extends into the gap. A first contact stop is positioned in the gap to define a critical gap distance limiting movement of the member of predetermined thickness in the gap. A base has a mounting surface, a port through the base and extending to the mounting surface. The port includes a first length having a smaller diameter at the mounting surface and a second length displaced from the mounting surface and having a larger diameter. A rigid cannula extends from the base through the port. The rigid cannula has a diameter smaller than the smaller diameter of the port, and the first length of the port has an annular open gap for lateral or pivotal movement of the rigid cannula. A mount of elastomeric material in the length having the larger diameter mounts the rigid cannula. The cannula includes hydrogel material in a desiccated state coating the surface of the cannula, including the beveled end, which rehydrates upon placement in the patient.

25 Claims, 6 Drawing Sheets

(56) References Cited

U.S. PATENT DOCUMENTS

| | | | |
|---|---|---|---|
| 4,373,527 A | 2/1983 | Fischell | 128/260 |
| 4,449,893 A | 5/1984 | Beckman et al. | 417/322 |
| 4,468,221 A | 8/1984 | Mayfield | 604/152 |
| 4,469,481 A | 9/1984 | Kobayashi | 604/67 |
| 4,565,542 A | 1/1986 | Berg | 604/131 |
| 4,596,575 A | 6/1986 | Rosenberg et al. | 604/891 |
| 4,650,469 A | 3/1987 | Berg et al. | 604/131 |
| 4,685,903 A | 8/1987 | Cable et al. | 604/154 |
| 4,734,092 A | 3/1988 | Millerd | 604/67 |
| 4,871,351 A | 10/1989 | Feingold | 604/66 |
| 4,886,499 A | 12/1989 | Cirelli et al. | 604/131 |
| 4,898,578 A | 2/1990 | Rubalcaba, Jr. | 604/66 |
| 4,944,659 A | 7/1990 | Labbe et al. | 417/413.2 |
| 5,085,562 A * | 2/1992 | van Lintel | 417/413.3 |
| 5,205,819 A * | 4/1993 | Ross et al. | 604/67 |
| 5,219,278 A | 6/1993 | Van Lintel | 417/413.1 |
| 5,224,843 A | 7/1993 | Van Lintel | 417/413.2 |
| 5,271,724 A | 12/1993 | Van Lintel | 417/413.2 |
| 5,277,556 A | 1/1994 | VanLintel | 417/413.2 |
| 5,328,460 A | 7/1994 | Lord et al. | 604/67 |
| 5,338,157 A | 8/1994 | Blomquist | 417/2 |
| 5,376,070 A | 12/1994 | Purvis | 604/31 |
| 5,433,710 A | 7/1995 | Van Antwerp | 604/152 |
| 5,443,508 A | 8/1995 | Giampapa | 623/11 |
| 5,480,386 A | 1/1996 | Brohy et al. | 604/131 |
| 5,485,408 A | 1/1996 | Blomquist | 364/578 |
| 5,507,737 A | 4/1996 | Palmskog | 604/891.1 |
| 5,569,186 A | 10/1996 | Lord et al. | 604/67 |
| 5,569,187 A | 10/1996 | Kaiser | 604/67 |
| 5,575,770 A | 11/1996 | Melsky et al. | 604/93 |
| 5,582,593 A | 12/1996 | Hultman | 604/65 |
| 5,630,710 A | 5/1997 | Tune et al. | 417/326 |
| 5,637,095 A | 6/1997 | Nason et al. | 604/135 |
| 5,658,250 A | 8/1997 | Blomquist et al. | 604/65 |
| 5,665,070 A | 9/1997 | McPhee | 604/131 |
| 5,695,473 A | 12/1997 | Olsen | 604/153 |
| 5,707,361 A | 1/1998 | Slettenmark | 604/131 |
| 5,725,363 A | 3/1998 | Bustgens et al. | 417/413.1 |
| 5,759,014 A | 6/1998 | Van Lintel | 417/413.3 |
| 5,759,015 A | 6/1998 | Van Lintel et al. | 417/322 |
| 5,761,782 A | 6/1998 | Sager | 29/25.35 |
| 5,764,159 A | 6/1998 | Neftel | 340/870.09 |
| 5,773,913 A | 6/1998 | Casselden | 310/338 |
| 5,788,669 A | 8/1998 | Peterson | 604/65 |
| 5,798,600 A | 8/1998 | Sager et al. | 310/330 |
| 5,807,375 A | 9/1998 | Gross et al. | 604/890.1 |
| 5,810,015 A | 9/1998 | Flaherty | 128/899 |
| 5,848,991 A | 12/1998 | Gross et al. | 604/140 |
| 5,858,005 A | 1/1999 | Kriesel | 604/180 |
| 5,931,814 A | 8/1999 | Alex et al. | 604/153 |
| 5,935,099 A | 8/1999 | Peterson et al. | 604/65 |
| 5,954,058 A | 9/1999 | Flaherty | 128/899 |
| 5,957,890 A | 9/1999 | Mann et al. | 604/131 |
| 5,957,895 A | 9/1999 | Sage et al. | 604/131 |
| 5,961,492 A | 10/1999 | Kriesel et al. | 604/32 |
| 5,997,263 A | 12/1999 | Van Lintel et al. | 417/413.2 |
| 5,997,501 A | 12/1999 | Gross et al. | 604/65 |
| 6,024,340 A * | 2/2000 | Lazarus et al. | 251/129.06 |
| 6,106,498 A | 8/2000 | Friedli et al. | 604/153 |
| 6,174,300 B1 | 1/2001 | Kriesel et al. | 604/132 |
| 6,237,619 B1 | 5/2001 | Maillefer et al. | 137/15.18 |
| 6,248,093 B1 | 6/2001 | Moberg | 604/131 |
| 6,259,587 B1 | 7/2001 | Sheldon et al. | 361/23 |
| 6,309,189 B1 | 10/2001 | Rey-Mermet et al. | 417/413.3 |
| 6,368,079 B2 * | 4/2002 | Peters et al. | 417/413.2 |
| 6,375,638 B2 | 4/2002 | Nason et al. | 604/132 |
| 6,390,791 B1 | 5/2002 | Maillefer et al. | 417/413.3 |
| 6,423,035 B1 | 7/2002 | Das et al. | 604/155 |
| 6,428,289 B1 * | 8/2002 | Lishanski et al. | 417/415 |
| 6,458,102 B1 | 10/2002 | Mann et al. | 604/131 |
| 6,461,331 B1 | 10/2002 | Van Antwerp | 604/131 |
| 6,485,461 B1 | 11/2002 | Mason et al. | 604/132 |
| 6,488,652 B1 | 12/2002 | Weijand et al. | 604/93.01 |
| 6,581,638 B2 * | 6/2003 | Frisch et al. | 137/596.17 |
| 6,585,695 B1 | 7/2003 | Adair et al. | 604/183 |
| 6,589,229 B1 * | 7/2003 | Connelly et al. | 604/890.1 |
| 6,589,299 B2 | 7/2003 | Missling et al. | 29/623.5 |
| 6,595,756 B2 | 7/2003 | Gray et al. | 417/44.1 |
| 6,645,142 B2 | 11/2003 | Braig et al. | 600/300 |
| 6,656,148 B2 | 12/2003 | Das et al. | 604/67 |
| 6,656,158 B2 | 12/2003 | Mahoney et al. | 604/131 |
| 6,656,159 B2 | 12/2003 | Flaherty | 604/131 |
| 6,669,669 B2 | 12/2003 | Flaherty et al. | 604/132 |
| 6,692,457 B2 | 2/2004 | Flaherty | 604/67 |
| 6,699,218 B2 | 3/2004 | Flaherty et al. | 604/131 |
| 6,716,002 B2 | 4/2004 | Higashino | 417/413.2 |
| 6,719,739 B2 | 4/2004 | Verbeek et al. | 604/288.04 |
| 6,723,072 B2 | 4/2004 | Flaherty et al. | 604/131 |
| 6,740,059 B2 | 5/2004 | Flaherty | 604/67 |
| 6,740,072 B2 | 5/2004 | Starkweather et al. | 604/504 |
| 6,749,587 B2 | 6/2004 | Flaherty | 604/151 |
| 6,752,787 B1 | 6/2004 | Causey et al. | 604/131 |
| 6,768,425 B2 | 7/2004 | Flaherty et al. | 340/870.07 |
| 6,770,067 B2 | 8/2004 | Lorenzen et al. | 604/891.1 |
| 6,774,437 B2 | 8/2004 | Bryant et al. | 257/350 |
| 6,809,653 B1 | 10/2004 | Mann et al. | 340/870.28 |
| 6,827,559 B2 | 12/2004 | Peters et al. | 417/413.2 |
| 6,827,702 B2 | 12/2004 | Lebel et al. | 604/67 |
| 6,830,558 B2 | 12/2004 | Flaherty et al. | 604/67 |
| 6,843,782 B2 | 1/2005 | Gross et al. | 604/141 |
| 6,852,104 B2 | 2/2005 | Blomquist | 604/504 |
| 6,878,132 B2 | 4/2005 | Kipfer | 604/111 |
| 6,948,918 B2 | 9/2005 | Hansen | 417/395 |
| 6,960,192 B1 | 11/2005 | Flaherty et al. | 604/181 |
| 6,974,437 B2 | 12/2005 | Lebel et al. | 604/65 |
| 6,986,649 B2 | 1/2006 | Dai et al. | 417/413.2 |
| 7,005,078 B2 | 2/2006 | Van Lintel et al. | 604/504 |
| 7,018,360 B2 | 3/2006 | Flaherty et al. | 604/123 |
| 7,029,455 B2 | 4/2006 | Flaherty | 604/131 |
| 7,040,335 B1 | 5/2006 | Ransom | 135/901 |
| 7,052,251 B2 | 5/2006 | Nason et al. | 417/321 |
| 7,107,086 B2 | 9/2006 | Reihl et al. | 600/310 |
| 7,115,111 B2 | 10/2006 | Haindl | 604/158 |
| 7,122,005 B2 | 10/2006 | Shusterman | 600/300 |
| 7,128,727 B2 | 10/2006 | Flaherty et al. | 604/131 |
| 7,128,730 B2 | 10/2006 | Marano-Ford et al. | 604/167.05 |
| 7,137,964 B2 | 11/2006 | Flaherty | 604/67 |
| 7,141,023 B2 | 11/2006 | Diermann et al. | 600/573 |
| 7,144,384 B2 | 12/2006 | Gorman et al. | 604/131 |
| 7,179,226 B2 | 2/2007 | Crothall et al. | 600/300 |
| 7,186,236 B2 | 3/2007 | Gibson et al. | 604/93.01 |
| 7,193,521 B2 | 3/2007 | Moberg et al. | 340/679 |
| 7,195,609 B2 | 3/2007 | Huegli | 604/67 |
| 7,204,823 B2 | 4/2007 | Estes et al. | 604/65 |
| 7,218,968 B2 | 5/2007 | Condie et al. | 607/59 |
| 7,255,690 B2 | 8/2007 | Gray et al. | 604/891.1 |
| 7,258,253 B2 | 8/2007 | Nicol et al. | 222/420 |
| 7,268,466 B2 | 9/2007 | Rasmussen | 310/328 |
| 7,275,522 B2 | 10/2007 | Beilharz et al. | 123/490 |
| 7,284,962 B2 | 10/2007 | Blakey | 417/53 |
| 7,287,965 B2 | 10/2007 | Vogeley et al. | 417/413.2 |
| 7,290,993 B2 | 11/2007 | Vogeley et al. | 417/413.2 |
| 7,291,110 B2 | 11/2007 | Sahatjian | 600/439 |
| 7,297,111 B2 | 11/2007 | Iliff | 600/300 |
| 7,300,402 B2 | 11/2007 | Iliff | 600/300 |
| 7,303,549 B2 | 12/2007 | Flaherty et al. | 604/181 |
| 7,306,560 B2 | 12/2007 | Iliff | 600/300 |
| 2002/0029776 A1 | 3/2002 | Blomquist | 128/200.11 |
| 2002/0040208 A1 | 4/2002 | Flaherty et al. | 604/288.01 |
| 2003/0014011 A1 | 1/2003 | Robert | 604/128 |
| 2003/0055380 A1 | 3/2003 | Flaherty | 604/155 |
| 2003/0163088 A1 | 8/2003 | Blomquist | 604/131 |
| 2004/0078028 A1 | 4/2004 | Flaherty et al. | 604/892.1 |
| 2004/0092873 A1 | 5/2004 | Moberg | 604/131 |
| 2004/0116866 A1 | 6/2004 | Gorman et al. | 604/93.01 |
| 2004/0158230 A1 | 8/2004 | Hunn et al. | 604/523 |
| 2004/0204673 A1 * | 10/2004 | Flaherty | 604/65 |
| 2004/0220551 A1 | 11/2004 | Flaherty et al. | 604/890.1 |
| 2004/0235446 A1 | 11/2004 | Flaherty et al. | 604/67 |
| 2004/0260233 A1 | 12/2004 | Garibotto et al. | 604/67 |
| 2005/0021005 A1 * | 1/2005 | Flaherty et al. | 604/890.1 |
| 2005/0022274 A1 | 1/2005 | Campbell et al. | 705/2 |
| 2005/0043676 A1 | 2/2005 | Remde et al. | 604/65 |
| 2005/0065464 A1 | 3/2005 | Talbot et al. | 604/66 |

(56) References Cited

U.S. PATENT DOCUMENTS

| | | | |
|---|---|---|---|
| 2005/0065760 A1 | 3/2005 | Murtfeldt et al. | 703/11 |
| 2005/0090808 A1 | 4/2005 | Malave et al. | 604/890.1 |
| 2005/0137573 A1 | 6/2005 | McLaughlin | 604/504 |
| 2005/0159708 A1 | 7/2005 | Sidler | 604/132 |
| 2005/0171512 A1 | 8/2005 | Flaherty | 604/890.1 |
| 2005/0177137 A1 | 8/2005 | Kipler | 604/65 |
| 2005/0182366 A1 | 8/2005 | Vogt et al. | 604/131 |
| 2005/0182391 A1 | 8/2005 | Schiltges et al. | 705/2 |
| 2005/0197625 A1 | 9/2005 | Haueter et al. | 604/131 |
| 2005/0215982 A1 | 9/2005 | Malave et al. | 604/890.2 |
| 2005/0222645 A1 | 10/2005 | Malave et al. | 607/60 |
| 2005/0238507 A1 | 10/2005 | DiIanne et al. | 417/415 |
| 2005/0273080 A1 | 12/2005 | Paul | 604/890.1 |
| 2006/0031094 A1 | 2/2006 | Cohen et al. | 600/300 |
| 2006/0036134 A1 | 2/2006 | Tarassenko et al. | |
| 2006/0041229 A1 | 2/2006 | Garibotto et al. | 604/122 |
| 2006/0047538 A1 | 3/2006 | Condurso et al. | 705/3 |
| 2006/0074381 A1 | 4/2006 | Malave et al. | 604/93.01 |
| 2006/0116664 A1 | 6/2006 | Richter et al. | 604/892.1 |
| 2006/0131530 A1* | 6/2006 | East | 251/129.06 |
| 2006/0137695 A1 | 6/2006 | Hellwig et al. | 128/898 |
| 2006/0147325 A1* | 7/2006 | Vogeley | 417/413.2 |
| 2006/0178633 A1 | 8/2006 | Garibotto et al. | 604/155 |
| 2006/0282290 A1 | 12/2006 | Flaherty et al. | 705/2 |
| 2007/0090321 A1* | 4/2007 | Bork | 251/335.2 |
| 2007/0118405 A1 | 5/2007 | Campbell et al. | 705/2 |
| 2007/0129688 A1 | 6/2007 | Scheurer et al. | 604/263 |
| 2007/0181425 A1 | 8/2007 | Kim | 204/403.11 |
| 2007/0219480 A1 | 9/2007 | Kamen et al. | 604/20 |
| 2007/0233206 A1 | 10/2007 | Frikart et al. | 607/60 |
| 2007/0251835 A1 | 11/2007 | Mehta et al. | 205/783 |
| 2007/0253021 A1 | 11/2007 | Mehta | 358/1.15 |
| 2007/0253380 A1 | 11/2007 | Jollota et al. | 370/338 |
| 2007/0254593 A1 | 11/2007 | Jollota et al. | 455/67.11 |
| 2007/0255116 A1 | 11/2007 | Mehta et al. | 600/300 |
| 2007/0255126 A1 | 11/2007 | Moberg et al. | 600/365 |
| 2007/0255250 A1 | 11/2007 | Moberg et al. | 604/503 |
| 2007/0255348 A1 | 11/2007 | Holtzclar | 607/60 |
| 2007/0258395 A1 | 11/2007 | Jollota et al. | 370/310 |
| 2008/0086086 A1 | 4/2008 | Field et al. | 604/123 |
| 2008/0119705 A1 | 5/2008 | Patel et al. | 600/347 |
| 2008/0161754 A1 | 7/2008 | Marano-Ford et al. | 604/67 |

OTHER PUBLICATIONS

U.S. Appl. No. 11/548,238, filed Oct. 10, 2006.
U.S. Appl. No. 11/618,682, filed Dec. 29, 2006.

* cited by examiner

APPARATUS FOR INFUSING LIQUID TO A BODY

BACKGROUND OF THE INVENTIONS

The field of the present invention is infusion systems.

Today, diabetes is understood to be reaching epidemic proportions in the United States. It remains as a worldwide problem as well. Diabetes brings with it a host of medical problems which are aggravated by conventional medicament dosage schemes. Traditional shots and the like are intermittent which can induce a cyclical plethora and paucity of medicament, typically insulin. Recent efforts have been undertaken to eliminate such harmful cyclical variations through continuous administration of medicament. Additionally, devices and controls have been designed to provide both a basal rate for sustained infusion and periodic boluses to accommodate the ingestion of carbohydrates. With these advantageous capabilities, enhanced designs taking into account considerations regarding cost, portability, longevity and accuracy of dispensation remain of interest.

A wide variety of prior systems having applicable components and processes exist. Reference is made to U.S. Pat. Nos. 4,898,578; 5,205,819; 5,630,710; 6,645,142; 6,852,104; and 7,018,360. Reference is also made to U.S. Patent Publications Nos. 2002/0029776; 2003/0032867; 2003/0163088; 2004/0220551; and 2005/0137573. The disclosures of the foregoing patents and patent publications are incorporated herein by reference.

In addition to the infusion of insulin for diabetes, infusion is useful for other purposes in bodies of both humans and animals. The types of liquids that can be delivered include, but are not limited to, insulin, antibiotics, nutritional fluids, total parenteral nutrition or TPN, analgesics, morphine, hormones or hormonal drugs, gene therapy drugs, anticoagulants, analgesics, cardiovascular medications, AZT and chemotherapeutics. The types of medical conditions treatable by infusion include, but are not limited to, diabetes, cardiovascular disease, pain, chronic pain, cancer, AIDS, neurological diseases, Alzheimer's Disease, ALS, Hepatitis, Parkinson's Disease or spasticity.

Infused patients have increased mobility with portable infusion dispensing systems while achieving a more frequent or continuous dosing. Such systems have the potential for regulating dosing responsive to near term need and conditions, such as the intake of carbohydrates in the case of diabetes. Control of the dispensing process to achieve accurate dosing is a fundamental design criteria for such devices. Various approaches have been used to control pump parameters and flow with piezoelectric mechanisms. U.S. Pat. No. 6,986,649 uses valve control based on pressure. U.S. Pat. No. 7,258,253 uses a restrictive orifice. U.S. Pat. No. 7,290,993 uses electronic wave form control. The disclosures of these patents are incorporated herein by reference. Control and monitoring of piezoelectric systems accurately enough for infusion demands more than electronic input and needs performance feedback. Simple, reliable and inexpensive miniaturized systems not having expensive critical components and system complications remain advantageous.

Also of consideration with portable infusion dispensing systems is patient comfort. Such systems frequently require subcutaneous cannula. The solution has been to make the cannula of flexible material and use a rigid sharp pin through the cannula to place the device, then withdrawing the pin. Rigid cannula are less complicated to place but can induce discomfort with patient movement.

SUMMARY OF THE INVENTIONS

The present inventions are directed to apparatus for infusing liquid to a body. A system contemplates the employment of an infusion device including a piezoelectric driven pump. A rigid cannula is separately contemplated.

In a first aspect of the present invention, an infusion device includes a housing with a control portion and a reservoir portion with the two portions separable. Being separable, the more costly components can be reused, thereby reducing long term costs to the user.

The infusion device further includes a precise drive in the first aspect of the present invention. This drive includes a piezoelectric bender assembly, a limiter and a resilient device cooperating together to provide precise reciprocal motion. The piezoelectric bender has a first end fixed relative to the control portion, a second end movable relative to the first end and a member of predetermined thickness fixed to move with the second end. Through repeatedly electrifying the piezoelectric bender, precise reciprocal motion is achieved.

The limiter is of dimensionally stable material and includes a gap in the first aspect of the present invention. The member of predetermined thickness extends into the gap to define a stroke gap equal to the limiter gap less the predetermined thickness. The resilient device is engaged to move with the second end of the piezoelectric bender assembly. The resilient device acts in opposition to the bender assembly with the bender assembly exhibiting greater force than the resilient device when the bender assembly is electrified.

The resilient device has a resilient stroke greater than the stroke gap. This accommodates variations in the positioning of the control portion and the reservoir portion together. The member of the piezoelectric bender assembly is capable of a stroke driven by the piezoelectric bender which is greater than the stroke gap allowed by the limiter. This accommodates variations in the positioning of the piezoelectric bender relative to the control portion. With the member of predetermined thickness and the dimensionally stable limiter gap, the stroke gap can be precisely defined even with variations in substantially all other dimensions. As a result, assembly and use can be less precise without loss of precision in volumetric infusion.

A pump is engaged to move with the above resilient device during the stroke of the piezoelectric bender. The piezoelectric bender assembly and the limiter are mounted in the control portion for reuse. The resilient device and the pump are in the disposable reservoir portion to properly allocate expensive components for reuse and inexpensive components for disposal.

In a second separate aspect of the present inventions, an infusion system includes a precise drive for infusion. A piezoelectric bender assembly employs a piezoelectric cantilevered bender with one end fixed relative to the pump and the other end movable. A member of predetermined thickness is fixed to move with the free end. The member of predetermined thickness extends into the gap defined by a limiter of dimensionally stable material. One or more contact stops are positionable at a critical distance across the gap to limit the movement of the member of predetermined thickness. These contact stops can be precisely located and fixed in place to afford a stable stroke to the infusion pump with the only criticality being the gap defined by the limiter, including one or more contact stops.

In a third separate aspect of the present inventions, a precise drive for an infusion pump includes a piezoelectric bender assembly having a cantilevered bender with an member of predetermined thickness fixed to move with the free end of the bender. Contact stops are positionable and fixed at a critical distance apart to define a gap for the limiter. These contact stops input the strokes of the bender to accumulate volume pumped, provide feedback control and the like.

In a fourth separate aspect of the present inventions, an infusion device includes a base having a mounting surface. A port through the base extends to the mounting surface which has two lengths of different diameters. The length of smaller diameter extend to the mounting surface. A mount of elastomeric material is located in the length of larger diameter with the rigid cannula mounted therein. The length of smaller diameter has an annular open gap for lateral or pivotal movement of the rigid cannula. Through this mounting, discomfort associated with a rigid cannula is assuaged.

In a fifth separate aspect of the present invention, a system for infusing liquid to a body includes an infusion device having a source of infusion fluid, a delivery port to the body, a metering element coupled between the source of infusion fluid and the delivery port, a controller capable of programmable infusion rate and time sequences and a wireless communication device at the controller. The system further includes a remote control having a counter, an input to the counter and a wireless communication device for transmitting the input in the counter. The wireless communication devices provide a wireless link using a local area communication standard. The controller is capable of programming an infusion rate and time sequence to dispense a bolus of a volume corresponding to the input in the counter. The remote control provides mobility to a patient with no more than a keychain fob or pendant to accommodate a need for near term additional medication.

In a sixth separate aspect of the present invention, a system for infusing liquid to a body includes an infusion device having a source of infusion fluid, a delivery port to the body, a metering element coupled between the source of infusion fluid and the delivery port, a controller capable of programmable infusion rate and time sequences and a wireless communication device at the controller. The system further includes a remote control having a program for controlling the programmable infusion rate and time sequences and a portable communication link for loading the program on a computer for generating commands for the controller. Through the advantage of small electronic devices capable of being used as peripherals to almost any computer, a program for modifying the controller can be loaded on equipment easily employed by anyone with a modicum of computer literacy. Again, mobility is enhanced for the patient. With capability on the computer, direct transmission to the controller can be accomplished. Where that is not the case, the remote control can transmit reprogramming to the controller.

In a seventh separate aspect of the present inventions, combinations of these separate aspects are contemplated to further advantage.

Accordingly, it is an object of the present invention to provide improved infusion systems. Other and further objects and advantages will appear hereinafter.

DETAILED DESCRIPTION OF THE PREFERRED EMBODIMENTS

Turning in detail to a preferred embodiment of a system for infusing liquid to a body, the systems presented in U.S. patent application Ser. No. 11/548,238, filed Oct. 10, 2006, U.S. patent application Ser. No. 11/618,682, filed Dec. 29, 2007, U.S. Provisional Application No. 60/991,145, filed Nov. 29, 2007 and U.S. Provisional Application No. 60/992,243, filed Nov. 29, 2007 are contemplated for employment with this invention and the disclosures are incorporated herein by reference.

An infusion device, generally designated 10, includes a somewhat truncated oblong housing 12 with a preferably low profile and a flat base. Other shapes are possible and the base may have some concavity for conformance to a body shape. The housing 12 is divided into a control portion 14 and a reservoir portion 16. The control portion 14 is intended to be used for a number of infusions. The reservoir portion 16 is intended to be expended after one use. To this end, the control portion 14 and the reservoir portion 16 are separable. A second control portion 14 may complete the set for the purpose of recharging one control portion 14 while using the other. Under such circumstances, the control portions preferably have independent electronic identities such that remote equipment can distinguish between controllers but can also reference cooperation as being employed by the same patient.

The control portion 14 has a cover 18 with a flat panel and outwardly inclined sides. The cover 18 is bonded to a panel 24 unless the configuration includes a non-rechargeable battery which requires opening of the case. If non-rechargeable, a separate compartment with a separate door is advantageous even though the battery compartment may remain as part of the control portion. If rechargeable, charging may occur with external sealed contacts or through induction. The panel 24 continues the outwardly inclined sides about its periphery and additionally includes a depending flange 26 to engage the reservoir portion 16. The control portion 14 is fully sealed against water intrusion except for one or more access holes through the panel 24 inwardly of the depending flange 26. To avoid a buildup from battery out-gassing, a hydrophobic, gas permeable barrier may be present in a small port through the housing. A control cavity 28 is created by the cover 18 and the panel 24.

The reservoir portion 16 includes a reservoir cover 30 and a base 32. The reservoir cover 30 includes a depending flange 34 which fits within a peripheral flange 36 extending upwardly from the base 32. The depending flange 34 and peripheral flange 36 create a channel 38' about the reservoir portion 16 to receive the depending flange 26 of the control portion 14. This mating of the control portion 14 and the reservoir portion 16 through the positioning of the depending flange 26 in the channel 38 is preferably constructed to remain locked together during use of the infusion device 10. A ridge and groove engagement may be employed to create a physical overlap requiring resilient deformation of one part to achieve extraction of the control portion 14 from the reservoir portion 16. Other mechanical means can be used as well.

To complete the profile of the housing 12, an overmold skirt 40 affixed to the peripheral flange 36 extends fully about the housing 12. The skirt 40 is similarly outwardly inclined to provide an overall profile which will not engage clothing and the like with activity of the patient.

Figure 1:
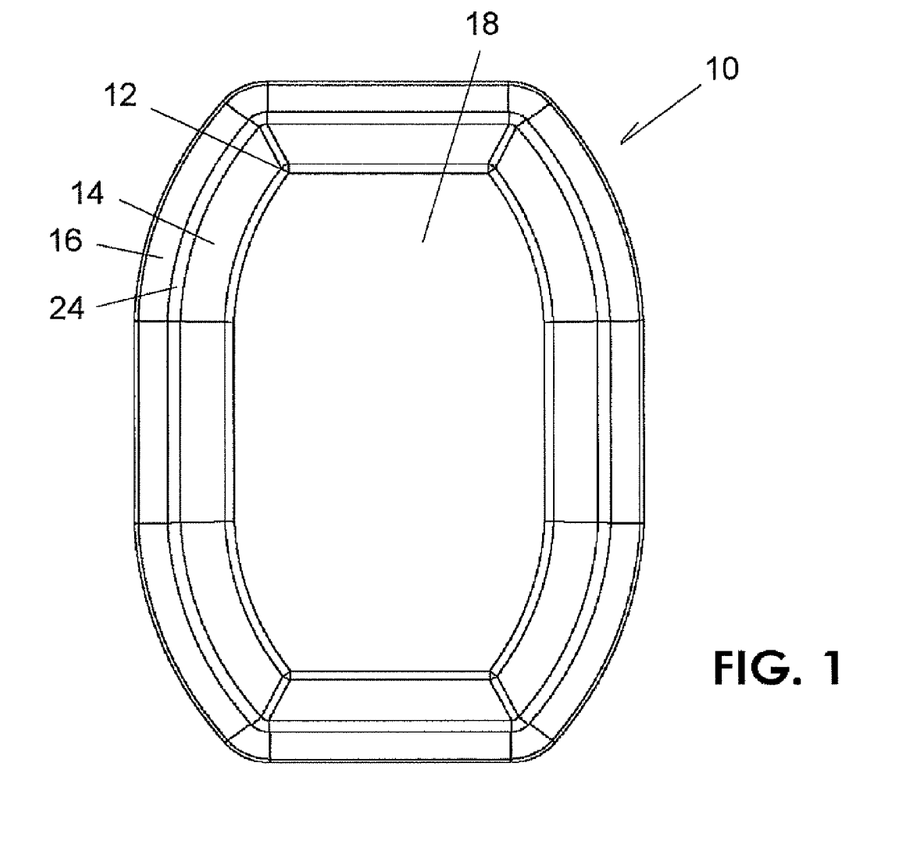
FIG. 1 is a plan view of the infusion device.
Figure 2:
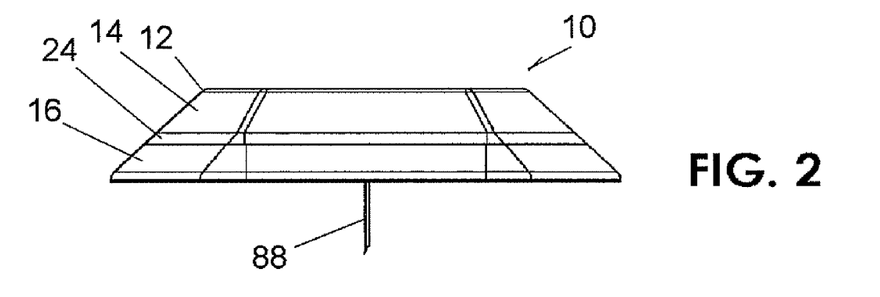
FIG. 2 is an end view of the infusion device.
Figure 3:
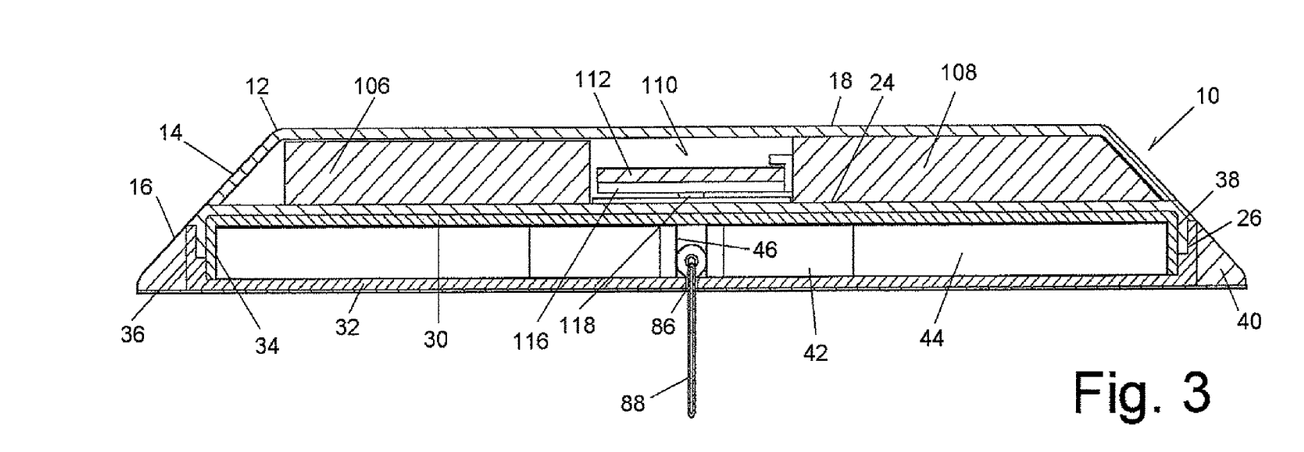
FIG. 3 is a cross-sectional elevation of FIG. 1.
Figure 4:
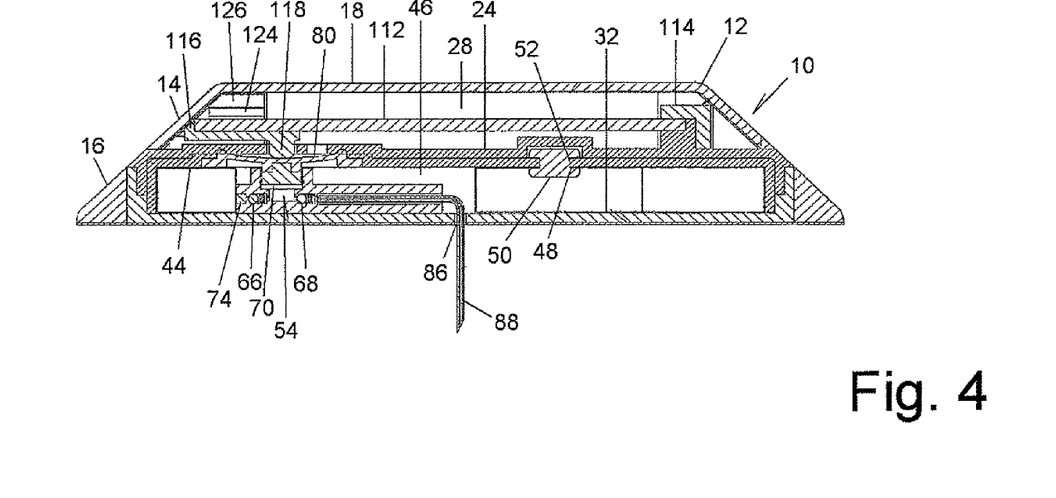
FIG. 4 is a cross-sectional elevation of FIG. 1.
Figure 4A:
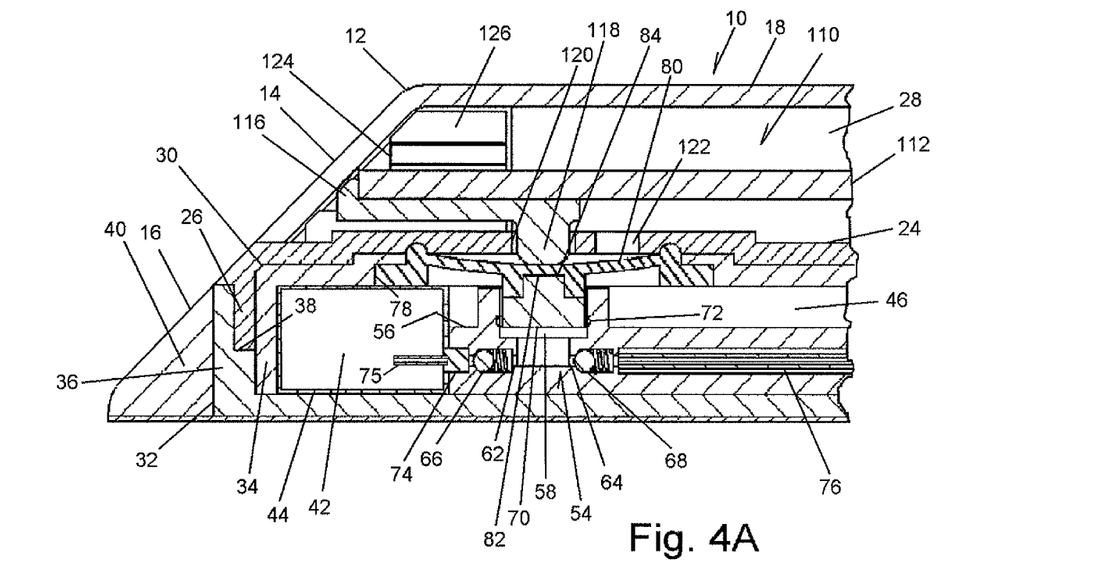
FIG. 4A is the cross-sectional elevation of FIG. 4 in greater detail.
Figures 5, 6:
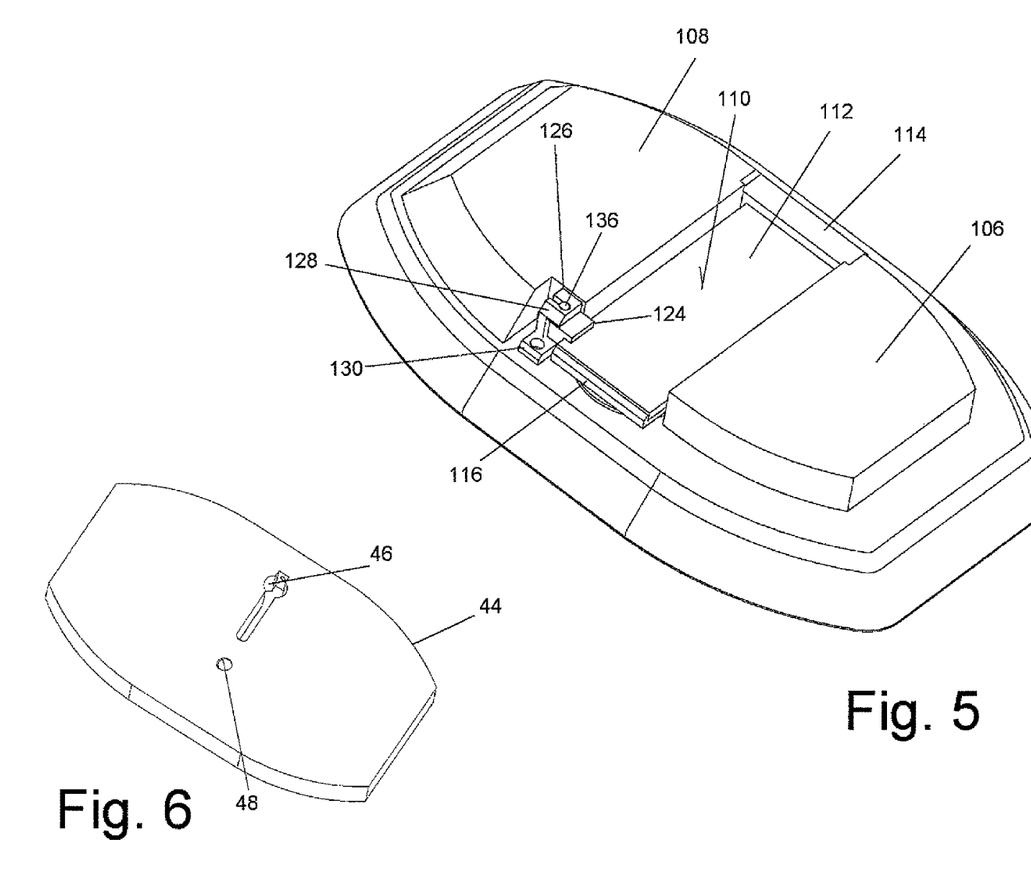
FIG. 5 is a perspective view of the infusion device with the cover removed.
FIG. 6 is a perspective view of the thin wall reservoir.
Figure 5A:
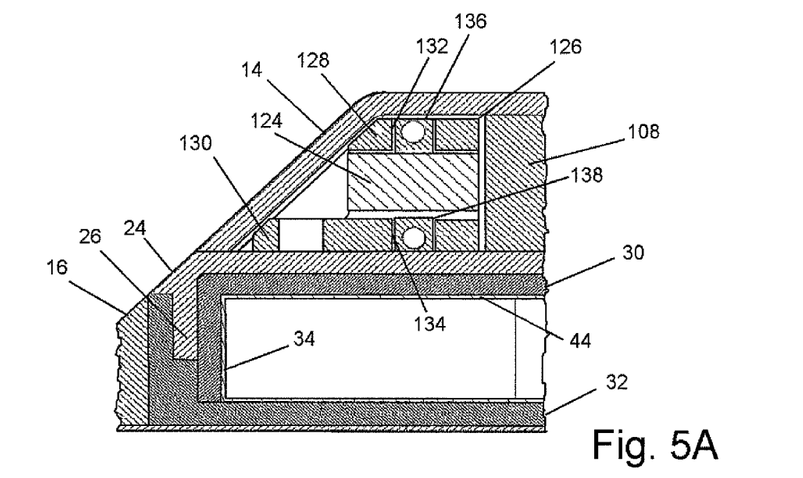
FIG. 5A is a cross-sectional elevation detail taken through the limiter.
Figure 7:
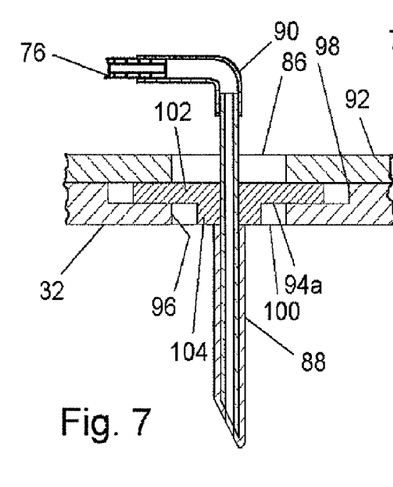
FIG. 7 is a cross-sectional elevation of a first mount of the cannula in the base of the infusion device.

The reservoir portion 16 defines a cavity between the reservoir cover 30 and the base 32. This cavity 42 includes a thin wall reservoir 44 which is illustrated in FIG. 6 in its fully inflated state which provides a source of infusion fluid. This reservoir 44 is able to collapse as liquid is dispensed therefrom. A cavity 46 in the thin wall reservoir 44 accommodates a pump, described below. A port 48 allows a charging of the reservoir 44. A plug 50 closes the port 48 as well as a port 52 open through the reservoir cover 30.

The cavity 42 of the reservoir portion 16 allows the thin wall reservoir 44 to contract as liquid is expended from the reservoir. The intent is to have the reservoir 44 filled with liquid without any gas or air and to keep it that way as the liquid is expended. To allow this, some venting into the cavity 46, outwardly of the thin wall reservoir 44, enables this contraction. Component fit may allow for such venting or separate hole through the body of the reservoir portion 16 may be specifically employed.

A pump, acting as a metering element and generally designated 54, is arranged within the reservoir portion 16 in the cavity 46 formed by the thin wall reservoir 44. The pump 54 includes a pump body 56 having a cylinder 58 open toward the control portion 14. The cylinder 58 includes a head portion of smaller diameter with an intake port 62 and an exhaust port 64 in communication therewith. The two ports 62, 64 are controlled through check valves 66, 68 defined by spring biased balls. The intake check valve 66 allows liquid to flow through the intake port 62 when the pressure differential between the reservoir 44 and the cylinder 58 is in the cylinder 58. The exhaust check valve 68 is opened when the pressure in the cylinder 58 increases above that beyond the exhaust port 64. A positive displacement element, in this embodiment a piston 70, is slidably arranged in the cylinder 58 to effect a pumping action. A piston seal 72 prevents leakage around the piston 70. A filter 74 allows liquid capillary flow therethrough while excluding air and other gases from entering the intake port 62. To overcome blockage of the filter 74 by a bubble of air, a thin tube 75 extends into the thin wall reservoir 44 from the filter 74 to beyond any bubble of a size likely to cover the filter 74 in order that liquid flow may be drawn through the thin tube. A tube 76 extends from the exhaust port 64 toward the center of the housing 12 to direct a charge of medicament to the patient.

A mounting hole 78 extends through the reservoir cover 30 to receive a resilient device which, in this embodiment, is a membrane spring 80. The membrane spring 80 is fixed to the reservoir cover 30 about its periphery. The membrane spring 80 includes a central portion with a cavity 82 to receive a boss 84 on the piston 70. The piston 70 is fixed to this central portion to move with the center of the membrane spring 80 in the cylinder 58.

The base 32 of the reservoir portion 16 defines a mounting surface with adhesive for retention on the patient. A port 86 extends through the base 32 at approximately the geometric center thereof.

In the first embodiment, the tube 76 is shown to be bent at a 90-degree angle to additionally form a cannula 88 as the ultimate delivery port to the body. The tube may conveniently be stainless steel or initial. The cannula 88 is preferably coated with a hydrogel which is retained in a desiccated state until insertion. This coating extends over the sharpened beveled end of the cannula with the lumen cleared. Once in place, the hydrogel swells when in contact with interstitial fluid to provide softer relief around the hard cannula 88. The hydrogel contemplated is in the nature of soft contact lenses. To provide greater comfort to the patient, four cannula embodiments are illustrated in FIGS. 7 through 10. In these embodiments, the cannula 88 is in communication with the tube 76 through a flexible elbow 90 rather than a bend in the tubing.

In each of these embodiments, the base 32 is shown to be laminated at least around the port 86 with an inner layer 92. The employment of this inner layer 92 allows for placement and capture of a mount 94 of elastomeric material. In each instance, the base 32 includes a port 86 which extends through to the mounting surface of the base. This port 86 has two lengths of differing diameter. The first length 96 extending to the mounting surface has a smaller diameter while the second length 98, displaced from the mounting surface, has a larger diameter. In all cases, there is an annular gap 100 outwardly of the cannula 88. This gap allows for angular movement and lateral movement of the cannula 88 relative to the base 32 without constraint from the periphery of the port 86.

The mounts 94 are unique in each of FIGS. 7 through 10. The mount 94a includes a disk 102 slidable within a cylindrical cavity forming the second length 98 of the port 86. The mount 94a is shown to include a smaller cylindrical disk 104 integral with the disk 102 which extends into the first length 96. The first length 96 is expanded in diameter to accommodate the disk 104 and retain the ability to define the annular gap 100. Thus, lateral and pivotal movement of the cannula 88 is possible with the mount 94a of FIG. 7, the material of the mount 94a being elastomeric.

Figure 8:
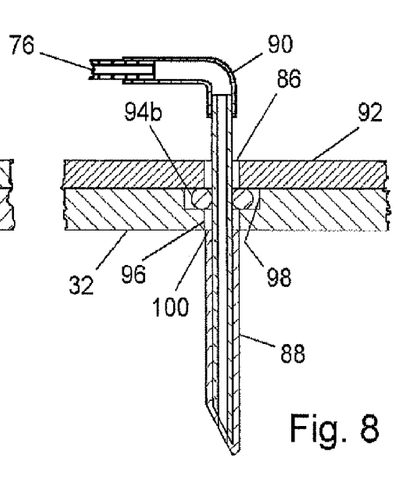
FIG. 8 is a cross-sectional elevation of a second mount of the cannula in the base of the infusion device.

In FIG. 8, the annular gap 100 is defined by the first length 96 and the cannula 88 of smaller diameter. An O-ring 94b is employed in the second length 98 about the cannula 88 to again allow for lateral and angular movement of the cannula 88 relative to the base 32.

Figure 9:
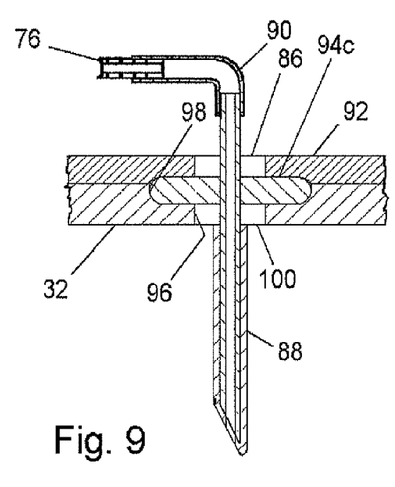
FIG. 9 is a cross-sectional elevation of a third mount of the cannula in the base of the infusion device.

In FIG. 9, a modified mount 94c is shown in an appropriate second length 98 of larger diameter. This mount 94c may include an interior cavity of gel rather than being solid elastomer in order to further accommodate lateral and angular movement of the cannula 88 within the port 86.

Figure 10:
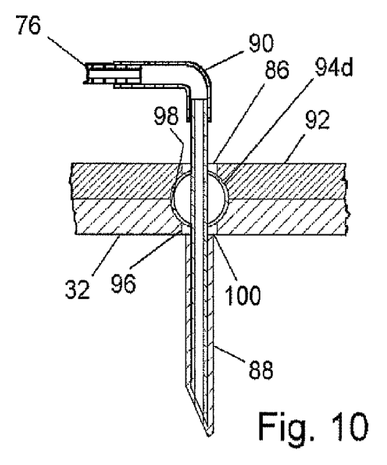
FIG. 10 is a cross-sectional elevation of a fourth mount of the cannula in the base of the infusion device.

Finally, FIG. 10 illustrates a mount 94d showing rotational movement of the cannula 88 without relying on mounting resilience. In this instance, the mount 94d is spherical within a spherical portion of the port 86. In all instances, the mount 94 resists the longitudinal motion of the cannula 88 therethrough to ensure full placement. The mounts 94 of FIGS. 7 and 9 can also be configured to allow longitudinal play of the cannula 88 without longitudinal movement of the cannula 88 through the mount 94.

Turning to the control portion 14, the control cavity 28 within the cover 18 and panel 24 provides room for a battery 106 and an electronics package 108. The electronics package 108 is powered by the battery 106 and includes a chip as a controller for control of pumping within the device 10. The electronics package 108 may also include a communication device, which is at minimum a wireless receiver and more preferably a transceiver. In this disclosure, the phrase "communication device" is employed to identify a transmitter, receiver or transceiver, as most appropriately understood from use. Other components such as employed in U.S. patent application Ser. No. 11/548,238 filed Oct. 10, 2006 are also contemplated.

A piezoelectric bender assembly, generally designated 110, is located between the battery 106 and the electronics package 108. The assembly 110 includes a cantilevered piezoelectric structural bender 112. At a first end of the bender 112, a mount 114 clamps the bender in combination with the panel 24 to maintain that end of the bender 112 fixed relative to the overall pump. The bender 112 is typically of bimetal construction with one layer powering the bender by being electrified to move the free end of the bender in one direction toward the membrane spring 80. The membrane spring 80 then restores the bender to its first position upon terminating the charge to the bender 112.

A bender tip 116 at the free end of the bender 112 is a block stably affixed to the bender 112. This tip 116 includes a finger 118 extending from one face of the bender against the center portion of the membrane spring 80. To engage the membrane spring 80, the finger 118 extends through the panel 24 at an opening 120. Additional holes 122 are shown through the panel 24 for leads to devices for sensing stroke. The bender tip 116 also covers the end of the piezoelectric bender 112. This tip 116 may be of dimensionally stable ceramic to insure continued calibration and minimal wear on reusable parts.

A member 124 extends from one edge of the bender 112 and has a specific thickness as measured in the direction of motion of the bender 112. The specific thickness of the member 124 may be fabricated to a specific value through machining or other process or may be accurately measured and later accommodated to account for the specific thickness measured. The member 124 may be of dimensionally stable ceramic as well.

A limiter 126 is affixed to the panel 24 and located within the control cavity 28. The limiter 126 is also of dimensionally stable material such as ceramic and includes a gap between two plates 128, 130. The member 124 extends to between the plates 128, 130 such that the motion of the bender 112 will be toward and away from alternate plates 128, 130 with each stroke and to define a stroke gap equal to the limiter gap less the predetermined thickness.

In the illustrated embodiment, each of the plates 128, 130 has a mounting hole 132, 134. These mounting holes 132, 134 are conveniently coaxial and are to either side of the gap defined by the plates 128, 130. They receive and affix contact stops 136, 138, respectively, through placement and bonding. Each of the stops 136, 138 allows a more precise location of one side of the gap defined between the plates 128, 130. With the employment of two holes 132, 134 and two stops 136, 138, both the size of the gap and the location of the gap in the direction of bender actuation can be controlled.

The size of the gap provides a specific stroke limit to the bender 112. The stroke of the bender 112 at the member 124 will then be the size of the precise gap defined by the contact stops 136, 138 less the thickness of the portion of the member 124 which is directly between the stops 136, 138. As a result, if the member 124 is of a predefined specific thickness, the gap between the contact stops 136, 138 can also be predefined. If the portion of the member 124 between the contact stops 136, 138 is of a predetermined but not predefined thickness, the contact stops 136, 138 must accommodate the intended stroke plus or minus the variation in the thickness of the member 124.

The need for a precise control of stroke is illustrated by an example. An appropriate single stroke dosage for U100 insulin is 0.05 units ($5 \times 10^{-4}$ ml.) having a weight of 0.00055 grams. Given the scale of the overall infusion device and resulting cylinder and piston size, the stroke which will give this single stroke dosage is on the order of 0.0050 of an inch, or 127 microns. Varying the bore of the cylinder 58 can change the appropriate stroke length to a small extent but not enough that a very precise ten percent overall tolerance of five ten thousands of an inch could vary significantly.

To achieve an appropriate stroke for the bender 112 without expensive requirements for close tolerance parts, the member 124 is either machined to a specific thickness or measured accurately. The limiter 126 is then gapped by locating the control stops 136, 138 in the mounting holes 132, 134 and placing a block of appropriate thickness between the stops 136, 138. The thickness of the gapping block is the appropriate stroke length of the bender 112 plus the thickness of the member 124.

The ability to place the stops 136, 138 for location of the gap in the direction of bender actuation is advantageous such that the bender assembly 110 need not be positioned relative to the gap with great precision. The cantilevered piezoelectric structural bender 112 is to be placed relative to the precise gap to reliably operate in a range of strong bending forces. It also is to be placed relative to the precise gap to impose an appropriate pretension on the membrane spring 80. The block used to precisely size the gap between the stops 136, 138 is placed relative to the location of the member 124 on the inner panel 24 to achieve these conditions.

The range through which the bender 112 exhibits strong bending force and the range through which the membrane spring 80 provides adequate restoring force and adequate preload on the bender 112 are accommodated firstly through design selection of the cantilevered piezoelectric structural bender 112 and of the membrane spring 80. Such selections are made so that the precise gap size is sufficiently smaller than the operative ranges of the bender 112 and the resilient membrane spring 80 to allow an acceptable placement tolerance for the bender 112. With an acceptable placement tolerance for the bender 112, only one hole 134 with one contact stop 138 may be employed in precise relationship with one plate 128 to define a precise gap for an appropriate pump stroke.

The contact stop 136 facing toward the membrane spring 80 when the device is assembled is appropriately arranged such that the membrane spring 80 retains some tension imposed by the finger 118 when the member 124 is against the contact stop 136. The selection of an appropriate length finger 118 is also to be considered to achieve this condition. By retaining some tension in the membrane spring 80, force remains to move the bender 112 through a full intake stroke. Additionally, having a sufficient amount of pretension in the membrane spring 80 accommodates the variations in placement of the control portion 14 with the reservoir portion.

The contact stop 138 facing away from the membrane spring 80 when the device is assembled is then positioned based on the foregoing gap requirements. The bender 112 is to be arranged and constructed with such capability that it will forcefully actuate through the stroke from the contact stop 136 to the contact stop 138. Indeed, it is appropriate for the bender 112 to have the capability when energized to move beyond the contact stop 138. In this way, a full stroke is assured between the contact stops 136, 138.

The contact stop 138 may include a device on or in the contact surface to sense recognition of the member 124. The sensor may sense proximity, complete a circuit or otherwise recognize the presence of the member 124. The member 124 may also have a sensor, a target or conductivity to allow recognition with the contact 138 of stroke completion. The data provided may be employed to de-energize the piezoelectric bender to save battery power and/or to count strokes. The contact stop 136 may also include such sensing as an assurance that the device is operating through full strokes.

In operation, the infusion device is configured as one or two control portions 14 and multiple reservoir portions 16. Each control portion 14 is reusable and potentially rechargeable through induction or external contacts. A second control portion 14 would allow recharging remotely from the patient without the need to suspend infusion. Each reservoir portion 16 operates to infuse a patent for up to seventy two hours. The patient would assemble the control portion 14 with one of the reservoir portions 16 for use.

Figure 11:
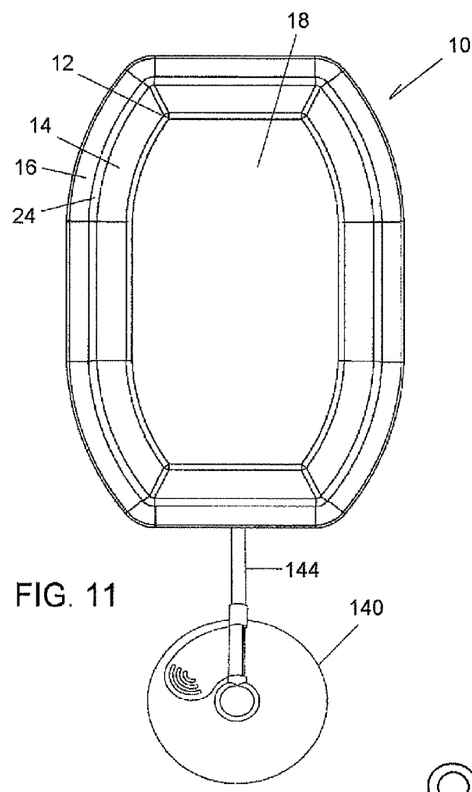
FIG. 11 is a plan view of an infusion device with a remote cannula.
Figure 12:
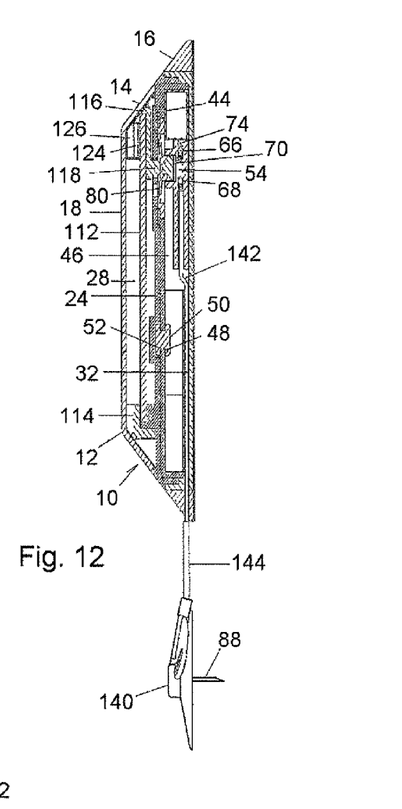
FIG. 12 is a section view of the infusion device of FIG. 11.

In the device of FIGS. 1-10, a plasticized sheet (not shown) is remove from the adhesive on the underside of the base 32 and the cannula 88 is exposed through the removal of a protective cover (not shown). The infusion device 10 would then be applied, either manually or through the use of an insertion device. If necessary, additional tape or bandaging to retain the device in place may be employed. In the embodiment of FIGS. 11 and 12, a remote port assembly 140 coupled with the infusion device 10 is shown. By using a remote port assembly 140, an inserter may be employed to position the cannula 88 without manual insertion by the patient. Such devices are disclosed in U.S. Pat. Nos. 6,926,694; 6,991,619; 6,991,620; 7,022,108; 7,128,730, the disclosures of which are incorporated herein by reference. A tube 142 extends from the infusion device 10 to couple with a flexible tube 144, which in turn is coupled with the remote port assembly 140.

Figure 13:
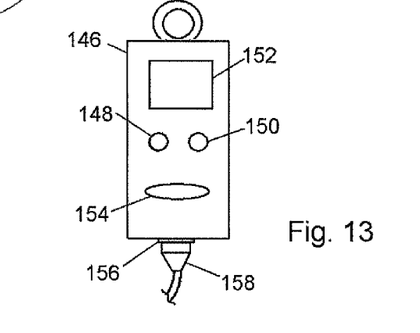
FIG. 13 is a front view of a remote control.

Activation of the controller of the electronics package 108 may be through schemes set forth in the disclosures incorporated herein by reference. Taps on the infusion device 10 can activate the controller 108. Control and communication through input through a cell phone or other electronic device capable of transmitting a message to the controller 108 can then be used to regulate dosage and bolus administrations, as needed. Alternatively, a dedicated and elementary remote control 146 can be employed for fully mobile access.

The remote control 146 preferably employs simple controls to avoid error but any number of features can be added to enhance user convenience. IR or a local area RF communication standard could be used to communicate. As a bolus is typically needed with the taking of food or drink, the remote control 146 is directed to that event in its most elemental form. Turning on the remote control 146 can be accomplished as in many personal devices by pushing any button. A bolus depends in magnitude on the amount of carbohydrates to be ingested and, consequently, needs volume control. A counter including a count-up button 148 and a count-down button 150 can be used to provide input to the remote control 146 to select a volume. Alternatively, a single toggle could be employed. A small LCD counter screen 152 can verify the count. A send button 154 can then transmit the count, representing a bolus volume, to the controller 108. These buttons can be recessed or covered with a hinged guard to protect against the sending of unintended signals to the controller 108. The control can be deactivated simply through a time delay when no button is pushed. Preferably, the signal transmitted includes identity information as well as bolus volume so that the controller 146 can verify that the signal is genuine. The remote 146 preferably can also be capable of receiving a return verification from the controller 108. The remote 146 can most conveniently be a keychain fob or pendent carried by the patient.

To provide more extensive mobility, the remote control 146 can additionally or alternatively include a memory with a program for controlling programmable infusion rate and time sequences in the controller 108. This could include commands regarding basal rates as well as boluses. A portable communication link including a communication device or a USB port 156 with a cable 158 or configured as a memory stick, as examples, can communicate universally with accessible computers for loading the program onto such a computer. The computer can then be used for generating or amending commands to the controller 108. The commands generated can then be communicated to the controller 108 either directly from the computer or through the remote control 146. Identification of the remote control 146 could also be transmitted to the computer to insure controller access.

Once activated with control instructions from one of the foregoing means or through preloading of the controller 108, the electronics can initiate timed electrifying of the piezoelectric bender with feedback through one or more sensors on the contact stops 136, 138 and/or member 124. With pumping through the piston 70, medicament is drawn from the thin wall reservoir 44 and infused through the cannula 88 into the patient. As medicament is depleted from the thin wall reservoir 44, the reservoir collapses until it approaches exhaustion. An integration of flow through monitoring of the pump 54 determines when the reservoir is becoming exhausted and initiates an alarm to signal the need for a replacement reservoir. The process then can be repeated through the removal of the reservoir portion 16 and replacement of a new reservoir portion 16 with the control portion 14 to continue infusion.

Thus, an improved method and apparatus for the infusion of liquid to a body is disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. An infusion device, comprising
   a housing including a control portion and a reservoir portion separable from the control portion;
   a precise drive including a piezoelectric bender assembly having a piezoelectric bender with a first end fixed relative to the control portion and a second end movable relative to the first end, a limiter fixed to the control portion including a first limiter end having a rest stop and a second limiter end having an actuator stop, the rest stop and the actuator stop defining a dimensionally stable limiter gap, the piezoelectric bender assembly extending into the limiter gap to define a stroke gap between the limiter and the piezoelectric bender assembly in the limiter gap, and a resilient device biased against the piezoelectric bender assembly to move with the piezoelectric bender assembly and having a resilient stroke greater than the stroke gap, the resilient device acting in opposition to the bender assembly with the bender assembly exhibiting greater force than the resilient device when the bender assembly is electrified, the piezoelectric bender assembly being capable of a stroke which is greater than the stroke gap allowed by the limiter;
   a pump including a cylinder and a piston capable of reciprocation in the cylinder, the piston engaged to move with the resilient device, the resilient device and the pump being in the reservoir portion.

2. The infusion device of claim 1, the resilient device biasing the piezoelectric bender assembly forcefully against the rest stop in the limiter gap when the piezoelectric bender is not electrified, the piezoelectric bender assembly being forcefully driven against the actuation stop in the limiter gap when the piezoelectric bender is electrified.

3. The infusion device of claim 2, the resilient device being a diaphragm having a periphery fixed relative to the reservoir portion and a central portion against which the piezoelectric bender assembly is in contact with the control portion and the reservoir portion assembled.

4. The infusion device of claim 2, the piston being coupled with the central portion of the resilient device with the resilient device being between the piezoelectric bender assembly and the piston.

5. The infusion device of claim 1, the piezoelectric bender assembly further having a member of predetermined thickness separately fabricated from the piezoelectric bender and affixed thereto, the member of predetermined thickness extending into the limiter gap, the stroke gap being equal to the limiter gap less the predetermined thickness.

6. The infusion device of claim 5, the member of predetermined thickness being of the dimensionally stable material of the limiter, the dimensionally stable material being a ceramic.

7. The infusion device of claim 1, the stroke gap being on the order of 0.0050 of an inch.

8. The infusion device of claim 1, the limiter including a sensor capable of registering the contact of the piezoelectric bender assembly with the actuator stop when the piezoelectric bender is electrified.

9. The infusion device of claim 1, the limiter having at least a first mounting hole extending to the gap and at least a first contact stop fixable in the at least first mounting hole at a position to define the limiter gap.

10. The infusion device of claim 9, the at least first mounting hole being two mounting holes extending to the gap and the at least first contact stop being two contact stops fixable in the mounting holes, respectively, at positions to define the limiter gap.

11. The infusion device of claim 9, the first contact stop and the bender assembly including sensor recognition of contact for sensing completion of a piezoelectric bender stroke.

12. The infusion device of claim 1 further comprising
a controller in the control portion in communication with the piezoelectric bender;
a reservoir in the reservoir portion, the pump being in communication with the reservoir and engaged to move with the resilient device;
a battery retained in the control portion in communication with the controller.

13. The infusion device of claim 12 further comprising
a wireless communication device at the controller;
a dedicated remote control in the form of a fob or pendent including a counter, an input to the counter and a wireless communication device for transmitting the input in the counter, the wireless communication device and the dedicated remote control providing a wireless link, the controller programming an infusion rate and time sequence to dispense a bolus of a volume corresponding to the input in the counter.

14. The infusion device of claim 1 further comprising
an infusion outlet from the reservoir portion and coupled with the pump, the infusion outlet including a cannula extending perpendicularly from the housing.

15. An infusion device, comprising
a housing including a control portion and a reservoir portion separable from the control portion;
a precise drive mounted in the control portion and including a piezoelectric bender assembly having a piezoelectric bender with a first end fixed to the control portion and a second end movable relative to the first end and a limiter including a first limiter end having a first stop and a second limiter end having a second stop, the first and second stops defining a dimensionally stable limiter gap there between, the limiter being fixed to the control portion, the piezoelectric bender assembly extending into the limiter gap to define a stroke gap between the limiter and the piezoelectric bender assembly in the limiter gap, the piezoelectric bender assembly being capable of a stroke which is greater than the stroke gap allowed by the limiter;
a pump including a cylinder and a piston capable of reciprocation in the cylinder, the piston engaged to move with the piezoelectric bender assembly.

16. The infusion device of claim 15, the piezoelectric bender assembly further having a member of predetermined thickness separately fabricated from the piezoelectric bender and affixed thereto, the member of predetermined thickness extending into the limiter gap, the stroke gap being equal to the limiter gap less the predetermined thickness.

17. The infusion device of claim 15, the limiter including a sensor capable of registering the contact of the piezoelectric bender assembly with the limiter when the piezoelectric bender is electrified.

18. The infusion device of claim 15, at least the first limiter end having a first mounting hole extending to the gap, the first stop including a first contact stop separate from the first limiter end and fixable in the first mounting hole at a position to define the limiter gap with the second stop.

19. The infusion device of claim 18, the first contact stop and the bender assembly including sensor recognition of contact for sensing completion of a piezoelectric bender stroke.

20. The infusion device of claim 15 further comprising
an infusion outlet from the reservoir portion and coupled with the pump, the infusion outlet including a cannula extending perpendicularly from the housing.

21. The infusion device of claim 15 further comprising
an infusion outlet from the reservoir portion and coupled with the pump, the infusion outlet including a cannula extending perpendicularly from the housing.

22. An infusion device, comprising
a housing including a control portion and a reservoir portion separable from the control portion;
a precise drive mounted in the control portion and including a piezoelectric bender assembly having a piezoelectric bender with a first end fixed to the control portion and a second end movable relative to the first end and a limiter including two limiter ends and two elements at the ends, respectively, defining a dimensionally stable limiter gap there between, the limiter being fixed to the control portion, the piezoelectric bender assembly extending into the limiter gap to define a stroke gap between the limiter and the piezoelectric bender assembly in the limiter gap, the piezoelectric bender assembly being capable of a stroke which is greater than the stroke gap allowed by the limiter;
a pump mounted in the reservoir portion, the pump including a cylinder, a piston capable of reciprocation in the cylinder and engaged to move with the piezoelectric bender assembly, a resilient diaphragm having a periphery fixed relative to the reservoir portion and a central portion against which the piezoelectric bender assembly is in contact, the piston being attached to the central portion of the resilient diaphragm and extending away from the piezoelectric bender assembly.

23. The infusion device of claim 22, the resilient diaphragm being biased against the piezoelectric bender assembly to move with the piezoelectric bender assembly and having a resilient stroke greater than the stroke gap, the resilient diaphragm biasing the piezoelectric bender assembly forcefully against one side of the limiter gap when the piezoelectric bender is not electrified, the piezoelectric bender assembly being forcefully driven against the other side of the limiter gap when the piezoelectric bender is electrified.

24. The infusion device of claim 22, one of the two limiter ends having a mounting hole extending to the gap, one of the two elements defining a contact stop separate from the mounting hole and fixable therein at a position to define the limiter gap with the other element.

25. The infusion device of claim 24, the contact stop and the bender assembly including sensor recognition of contact for sensing completion of a piezoelectric bender stroke.

* * * * *